United States Patent
Gulaka et al.

(10) Patent No.: US 9,355,449 B2
(45) Date of Patent: May 31, 2016

(54) SYSTEM AND METHOD FOR AUTOMATIC PLANNING OF TWO-DIMENSIONAL VIEWS IN 3D MEDICAL IMAGES

(71) Applicant: SAMSUNG ELECTRONICS CO., LTD., Suwon-si (KR)

(72) Inventors: Praveen Gulaka, Moscow (RU); Mikhail Yurievich Sirotenko, Moscow (RU); Dmitry Alexandrovich Korobchenko, Moscow (RU); Alexey Bronislavovich Danilevich, Moscow (RU); Mikhail Nikolaevich Rychagov, Moscow (RU)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 135 days.

(21) Appl. No.: 14/217,851

(22) Filed: Mar. 18, 2014

(65) Prior Publication Data
US 2014/0270433 A1 Sep. 18, 2014

(30) Foreign Application Priority Data
Mar. 18, 2013 (RU) ................... 2013111934

(51) Int. Cl.
| | | |
|---|---|---|
| *G06T 7/00* | (2006.01) | |
| *A61B 6/00* | (2006.01) | |
| *G09B 23/30* | (2006.01) | |
| *G06T 19/20* | (2011.01) | |
| *G09B 23/28* | (2006.01) | |
| *A61B 6/03* | (2006.01) | |

(52) U.S. Cl.
CPC .......... *G06T 7/0012* (2013.01); *A61B 6/5223* (2013.01); *G06T 7/0046* (2013.01); *G06T 7/0048* (2013.01); *G06T 19/20* (2013.01); *G09B 23/28* (2013.01); *G09B 23/30* (2013.01); *A61B 6/032* (2013.01); *G06T 2207/10072* (2013.01); *G06T 2207/20101* (2013.01); *G06T 2207/20124* (2013.01); *G06T 2210/41* (2013.01); *G06T 2219/008* (2013.01); *G06T 2219/028* (2013.01)

(58) Field of Classification Search
None
See application file for complete search history.

(56) References Cited

U.S. PATENT DOCUMENTS

| 7,711,160 B2 | 5/2010 | O'Donnell et al. |
|---|---|---|
| 2009/0060396 A1* | 3/2009 | Blessan ............... G06K 9/6212 382/317 |

(Continued)

OTHER PUBLICATIONS

Tobias Heimann, et al., "Statistical shape models for 3D medical image segmentation: A review", Medical Image Analysis, Aug. 1, 2009, pp. 543-563, vol. 13, No. 4, Oxford University Press.

(Continued)

*Primary Examiner* — Siamak Harandi
(74) *Attorney, Agent, or Firm* — Sughrue Mion, PLLC

(57) ABSTRACT

Provided is medical equipment and a technique for analyzing medical images. A method for automatically planning views in three-dimensional (3D) medical images includes: estimating a statistical model indicating positions of anatomical points, the statistical model having parameters calculated by minimizing energy of a loss function; training an anatomical point detector to detect the plurality of anatomical points by using the estimated statistical model; acquiring a 3D image having a region of interest; detecting a set of candidates of the anatomical points in the 3D image; searching the set of candidates for an optimal configuration corresponding to the plurality of anatomical points; and forming a view plane based on the optimal configuration found by the searching.

20 Claims, 6 Drawing Sheets

(56) References Cited

U.S. PATENT DOCUMENTS

| | | |
|---|---|---|
| 2011/0172516 A1 | 7/2011 | Sugiura |
| 2011/0206260 A1 | 8/2011 | Bergmans et al. |
| 2012/0070074 A1* | 3/2012 | Liu ...................... G06K 9/6257 382/159 |
| 2012/0121152 A1 | 5/2012 | Lu et al. |

OTHER PUBLICATIONS

Su-Lin Lee, et al., "Optimal Scan Planning with Statistical Shape Modelling of the Levator Ani", In: "Field Programmable Logic and Application", Jan. 1, 2003, pp. 714-721, vol. 2878, Springer Berlin Heidelberg.

Communication from the European Patent Office issued Aug. 28, 2014 in a counterpart European Application No. 14160590.7.

\* cited by examiner

SYSTEM AND METHOD FOR AUTOMATIC PLANNING OF TWO-DIMENSIONAL VIEWS IN 3D MEDICAL IMAGES

CROSS-REFERENCE TO RELATED APPLICATIONS

This application claims the benefit of Russian Patent Application No. 2013111934, filed on Mar. 18, 2013, in the Russian Patent Office, the disclosure of which is incorporated herein in its entirety by reference.

BACKGROUND

1. Field

One or more exemplary embodiments relate to medical equipment and a technique for analyzing medical images, and more particularly, to a system and method for automatically planning two-dimensional (2D) views in three-dimensional (3D) images.

2. Description of the Related Art

In practice, doctors may often require two-dimensional (2D) pictures of a region of interest to make a diagnosis. Existing devices, such as a magnetic resonance tomography (MRT) apparatus, a computed tomography (CT) apparatus, etc., may generate 3D images. Hence, it is necessary to search a 3D volume for 2D views suitable for a doctor's diagnosis. Depending on a region of interest and the type of an applied device, the search operation may last up to 20 minutes (for example, when the search operation involves an MRT of the heart). In addition to the large time expenditures, the search operation needs to be performed by highly skilled medical personnel; however, even in this case, pictures of the same organ, taken by two doctors, may differ from each other. Thus, a comparison of pictures of one patient taken at different times may be complicated.

A method of automatic planning of 2D pictures in 3D images is required to solve these problems. Several approaches to solve the problems have been proposed in recent years. The approaches may be classified by the type of the medical scanner (tomography) (e.g., MRT and CT), scanned part of a body (e.g., brain, heart, backbone, knee and shoulder), and type of algorithm (e.g., based on anatomical points, based on the segmentation, and based on the atlas and hybrid).

Algorithms based on anatomical points use anatomical points as milestones for constructing desired views. In this case, construction of the views is performed by searching for these anatomical points. Algorithms based on segmentation include performing segmentation of anatomical structures and building planes based on this segmentation. Atlas-based algorithms perform registration of an input image according to some atlas for which planes of a specified region of interest are known. Hybrid algorithms use a combination of two or more approaches.

U.S. Patent Application No. 2011/0206260 discloses a method of automated sequential planning of MRT pictures, including: acquiring a first survey image with a first field of view, the first survey image having a first spatial resolution, finding a first region of interest and at least one anatomical point in the first survey image, detecting a position and an orientation of the first region of interest which is used for planning of a second survey image, acquiring the second survey image with a second field of view, the second survey image having a new spatial resolution, the new spatial resolution being higher than the first spatial resolution, generating planning of a geometry for an anatomical region of interest using the second survey image, and acquiring a diagnostic image of the anatomical region of interest using the planned geometry. The main drawback of the method disclosed in U.S. Patent Application No. 2011/0206260 is that the method requires acquisition of several images that may be time consuming.

U.S. Pat. No. 7,711,160 discloses a method, system and device for determining optimal viewing planes in order to acquire a cardiac image. The method includes acquiring a set of sagittal, axial, and coronal images of a heart so that the axial and coronal images intersect orthogonally with the sagittal image, wherein an image of the heart actually has a natural axis and a left ventricle with a blood depot, and an edge of the blood depot and a peak. The method also includes making a map of edges of the blood depot and using a map for creating an axis of coordinates oriented along the natural axis. The main drawback of the method disclosed in U.S. Pat. No. 7,711,160 is that the method requires prior knowledge of a location of the heart in order to obtain three orthogonal images. The method is also based on algorithms for identification of edges which may not work well for quickly shot images having low signal-to-noise ratio and low quality.

U.S. Patent Application No. 2012/0070074 discloses a method and device for training an anatomical point detector that receives training data including positive training sets, each including a set of positively annotated instances, and negative training sets, each including at least one negatively annotated instance. A classification function is initialized by training a first weak qualifier based on the positive training sets and negative training sets. All training instances are evaluated using the classification function. A gradient of a loss function is calculated for each of a set of other qualifiers based on spatial context information of each instance in each positive training set evaluated by the classification function. A gradient associated with each of the remaining weak qualifiers is computed based on gradients of loss functions. A weak classifier having a lowest associated gradient value and a set weighting parameter and associated gradient value is then selected and added to the classification function. The main drawback of the method disclosed in U.S. Patent Application No. 2012/0070074 is that the method uses the spatial context information only locally by including regularization of a total variation in loss function. Use of relative global positions of anatomical points may improve the quality of detection of anatomical points.

SUMMARY

One or more exemplary embodiments disclosed herein provide a system and method for efficient automatic planning of two-dimensional (2D) views in three-dimensional (3D) medical images by optimally applying a statistical model both during training of an anatomical point detector and during construction of views based on detected points. The exemplary embodiments may achieve an enhanced method of automatic planning of views in 3D medical images, although it is understood that the exemplary embodiments are not required to achieve these benefits.

Additional aspects will be set forth in part in the description which follows and, in part, will be apparent from the description, or may be learned by practice of the presented exemplary embodiments.

According to one or more exemplary embodiments, there is provided a method of automatically planning views in 3D medical images including: estimating a statistical model indicating positions of anatomical points, the statistical model having parameters calculated by minimizing energy of a loss function; training an anatomical point detector to detect the anatomical points by using the estimated statistical model; acquiring a 3D image having a region of interest; detecting a set of candidates of the plurality of anatomical points in the 3D image; searching the set of candidates for an optimal configuration corresponding to the plurality of anatomical points; and forming a view plane based on the optimal configuration found by the searching.

The estimating of the statistical model may be performed using an annotated set of the 3D medical images.

The training of the anatomical point detector may be performed using energy of the estimated statistical model.

The detecting of the set of candidates of the anatomical points is performed by the anatomical point detector trained using an algorithm based on the plurality of anatomical points.

The searching of the set of candidates for the optimal configuration corresponding to the plurality of anatomical points includes performing a greedy iterative search to search for a configuration that minimizes energy of the estimated statistical model.

According to one or more exemplary embodiments a medical system configured to automatically plan views in 3D medical images may include: an image acquirer configured to acquire the 3D medical images;

a detector configured to detect anatomical points by using a statistical model having parameters calculated by minimizing energy of a loss function that is determined by using the equation:

$$\hat{L}(X, Y, Q, M_x, \Sigma_x) = \sum_{x \in X} L(y_x, q_x) + E(X, M_x, \Sigma_x)$$

in which Y denotes the binary mark taking a value of 1 if an input region of an image contains an anatomical point, and 0 if the input region does not contain an anatomical point, q has a value between 0 and 1 and represents a pseudo-probability, computed by an anatomical point detector, that the region contains an anatomical point. Yx and Qx are values of Y or Q at a coordinate point x, and 'x' is a space position or coordinates of all voxels in a volume; an updating block configured to update the anatomical points by performing a search algorithm for finding an optimal configuration of the anatomical points; a calculation block configured to acquire parameters of a view plane by applying parameters of a target view to an algorithm for transforming coordinates. Outputs of the detection unit that are positions of the anatomical points may be input to the updating block, and outputs of the updating block may be input to the calculation block.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1A:
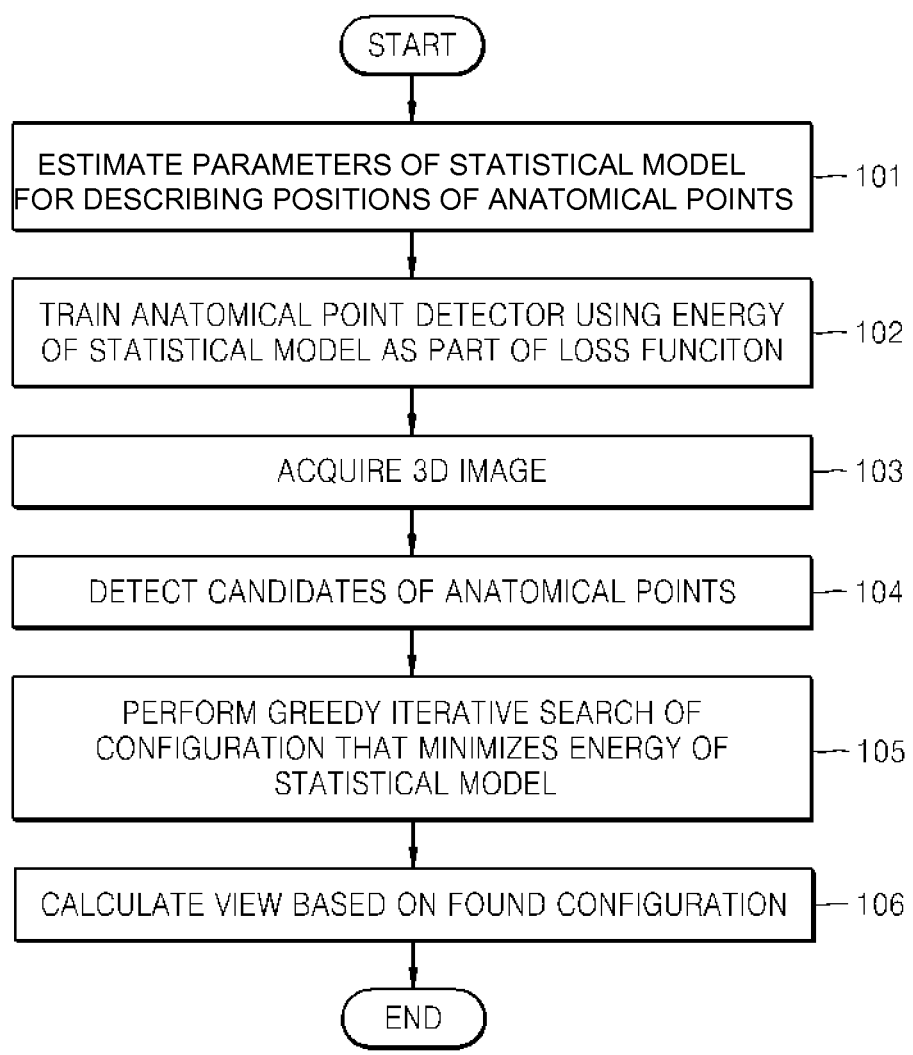
FIG. 1A is a flowchart of a method of automatically planning a view according to an exemplary embodiment.

Reference will now be made in detail to exemplary embodiments, examples of which are illustrated in the accompanying drawings, wherein like reference numerals refer to like elements throughout. In this regard, the exemplary embodiments may have different forms and should not be construed as being limited to the descriptions set forth herein. Accordingly, the exemplary embodiments are described below, by referring to the figures, to explain aspects of the present disclosure.

One or more exemplary embodiments relate to methods and systems based on detection of anatomical points. According to the exemplary embodiments, planning of required views is performed by calculating coordinates of a plane passing through a preset set of anatomical points. Most modern approaches use detectors for detecting anatomical points obtained by training on some training database consisting of input images and manually annotated anatomical points corresponding to a specified region of interest. Such detectors may be susceptible to a considerable number of inaccurate operations, especially in processing images of low quality. One of the reasons for such inaccurate operations is that training samples include only positive and negative samples. However, it may be difficult to determine the unique positions of anatomical points in real images. Thus, during training, inaccurate operations of a detector at a point that is close to a correct position of an anatomical point should be penalized less than incorrect operations at a point which is located far from the correct position. Some of the approaches described above may solve this problem only partially by adding smoothness conditions to loss functions. However, such approaches do not take into consideration a global correlation between anatomical points.

An additional element of the related art approaches lies in the generation of a statistical model including some parameters which are estimated based on data (such as mathematical expectation and mean-square deviation of positions of anatomical points) for a set region of interest. This statistical model may be used to estimate positions of anatomical points independently having or sharing some weak qualifier of images having outputs which are included in the statistical model. This approach may exhibit high efficiency only in data processing with a small number of non-standard cases since the approach aims at the formation of average decisions and does not strongly rely on weak qualifiers.

In some approaches, an attempt is made to overcome the above-described problems by constructing a more complex statistical model, but such approaches require an application that involves a complicated procedure for calculations of an output.

The method and system for automatically planning 2D views in 3D images according to the exemplary embodiments have several differences from related art methods and systems for automatic planning of views.

For example, the exemplary embodiments may use an anatomical point detector for detecting a set of candidates of anatomical points and a statistical model for performing a search to find an optimal configuration based on these candidates, which, in turn, may be used for constructing desired view planes.

Parameters of a specified statistical model may be estimated from a training sample which is used for training an anatomical point detector.

The specified statistical model may include a loss function used for training the anatomical point detector that provides improved quality of detection.

A fast greedy algorithm for finding a local minimum of a nonlinear loss function may be used at the last operation in order to find an optimal configuration from a set of candidates of anatomical points.

The method and system according to the exemplary embodiments may be used in combination with many different types of 3D medical imaging devices, such as, for example, a magnetic resonance tomography (MRT) apparatus, a computed tomography (CT) apparatus, etc., and with many different types of trained anatomical point detectors.

Figure 1B:
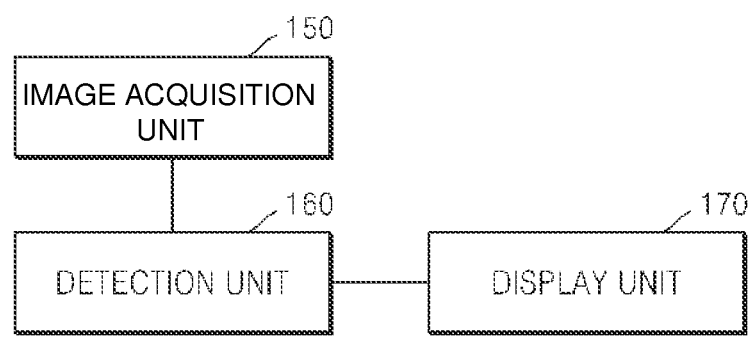
FIG. 1B is a block diagram of a system for automatically planning a view according to an exemplary embodiment.

FIG. 1A is a flowchart of a method of automatically planning a view according to an exemplary embodiment, and FIG. 1B is a block diagram of a medical system for automatically planning a view according to an exemplary embodiment.

Figure 2:
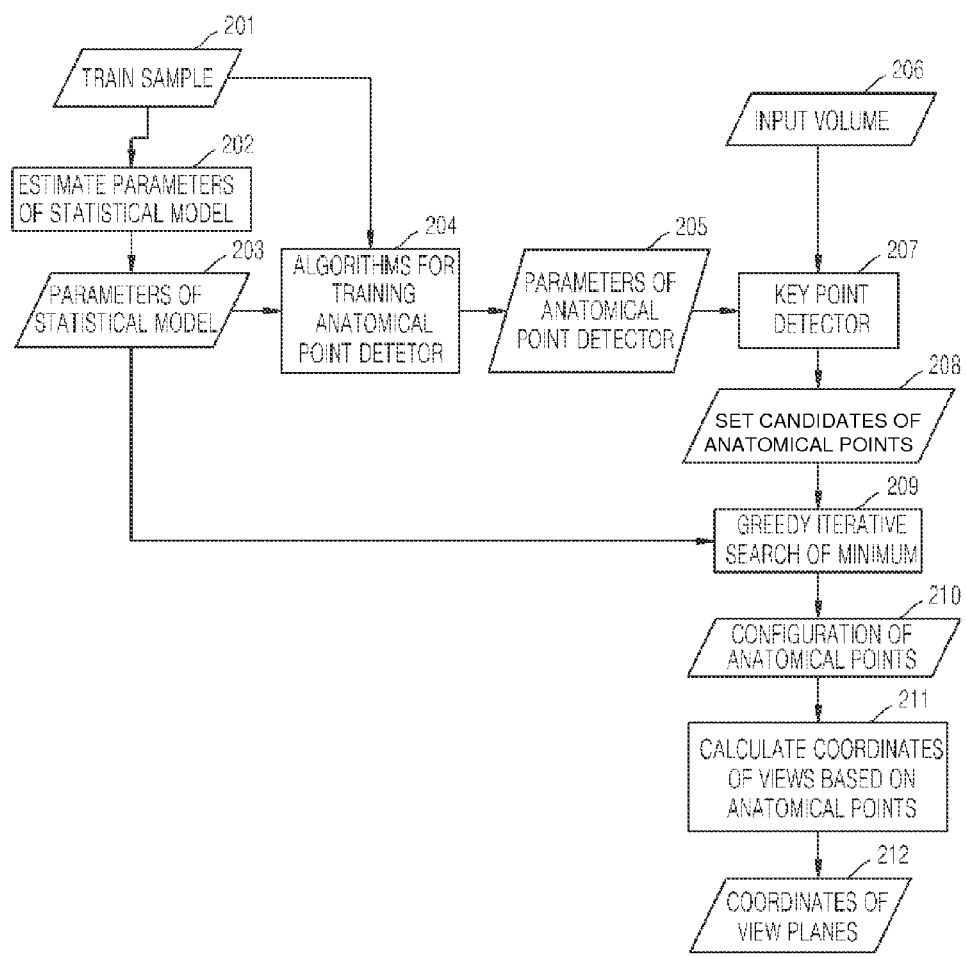
FIG. 2 is a data flow diagram according to an exemplary embodiment.

FIG. 2 illustrates a flow of data corresponding to the flowchart of FIG. 1A. Referring to FIG. 1A, the method may be divided into two main parts: operations 101 and 102 and operations 103 through 106.

Training and estimation of parameters (operations 101 and 102) are preliminary stages which are required to be performed only once for a set type of a procedure of planning a view.

In the method of automatically planning a view according to the present exemplary embodiment, parameters of a statistical model are estimated that describe positions of a plurality of anatomical points at operation 101.

An anatomical point detector is trained using the energy of the estimated statistical model as part of a loss function at operation 102.

A three-dimensional (3D) image having a region of interest is acquired at operation 103.

A set of candidates of the plurality of anatomical points are detected at operation 104. In detail, the set of candidates may be a set of points that may exist within a 3D image.

The detected set of candidates is searched for a configuration corresponding to the plurality of anatomical points at operation 105.

A view plane is calculated based on the configuration found in operation 105 at operation 106.

Referring to FIG. 1B, the medical system according to the present exemplary embodiment includes an image acquisition unit 150 (e.g., image acquirer), a detection unit 160 (e.g., detector), and a display unit 170 (e.g., display). The image acquisition unit 150 acquires a 3D medical image and transmits the same to the detection unit 160. The detection unit 160 detects anatomical points (landmarks) from a section of the 3D medical image and transmits the anatomical points to the display unit 170. The display unit 170 may display the anatomical points on a screen or transmit the same to another device.

In detail, detection of the anatomical points and planning of the view (operations 103 through 106) are used for planning views in each new 3D input image without the need to repeat operations 101 and 102.

In operation 101, the statistical model is set which describes positions of interconnected anatomical points, and parameters of the statistical model are estimated. Estimation of the parameters of the statistical model (202) is performed by analyzing a training sample (201) including a set of input 3D images and annotations of anatomical points corresponding to the input 3D images. The annotations of anatomical points may be obtained by setting coordinates of the anatomical points in a volume of a 3D image. In operation 102, an anatomical point detector (not shown) is trained by an average of a training algorithm (204) that uses the training sample (201) and the parameters of the statistical model (203).

In planning of views, a 3D image including a volume (206) is formed by the image acquisition unit 150, and the parameters contained in the statistical model that the anatomical point detector uses to detect candidates of anatomical points are input to the detection unit 160 for detecting anatomical points (207). Based on this set of anatomical points (208) and the statistical model, a greedy iterative search (209) is performed to find a local minimum of a loss function corresponding to some configuration of the anatomical points (210). Finally, coordinates of a view plane (212) are computed based on the detected coordinates of views based on anatomical points (211).

Statistical Model.

Any statistical model obtained by considering spatial relations between anatomical points may be generally used according to exemplary embodiments. The following Equation (1) may be used according to an exemplary embodiment:

$$E(X, M_x, \Sigma_x) = \sum_{x_s \in X, x_t \in X} \psi_{st}(x_s, x_t, M_x, \Sigma_x) \qquad \text{Equation (1)}$$

where $X \in \mathbb{R}^{a \times M}$ is a set of M vectors of coordinates of the anatomical points, which are called a configuration of anatomical points, $M_X$ is a mathematical expectation of distances of anatomical points from each other, $\Sigma_X$ is a tensor of covariance of distances between anatomical points, E is an energy of the statistical model, wherein smaller values of E match better with a configuration of anatomical points, and $\psi_{st}$ is a function of spatial energy that measures a statistical coordination of coordinates of two anatomical points.

According to an exemplary embodiment, the function $\psi_{st}$ may be determined according to Equation 2 as follows:

$$\psi_{st}(x_s, x_t, M_X, \Sigma_X) = 0.5(x_x - x_t - \mu_{st})^T \Sigma_{st}^{-1}(x_s - x_t - \mu_{st}) \qquad \text{Equation (2)}$$

where $x_t$ and $x_s$ are vectors of coordinates in a 3D space acquired from a configuration of anatomical points x, and $\mu_{st}$ is a three-element vector from the point s to the point t, which is a return matrix of a covariance of 3D vectors between the points s and t.

Training of an Anatomical Point Detector.

According to an exemplary embodiment, the anatomical point detector refers to an algorithm that receives a local region of an image as an input and generates as an output a vector representing either presence or absence of some anatomical point in the local region. According to an exemplary implementation of the algorithm, the vector may encode a pseudo-probability that the local region contains the anatomical point. Training of the anatomical point detector represents a process of an anatomical search of parameters in the algorithm. A general method of training an anatomical point detector includes collecting a training sample and starting an optimization algorithm that minimizes loss of some functions. The training sample is a set of 3D images for which coordinates of each anatomical point is known a priori. In an image in the set, any random region which is located near an anatomical point is considered a positive example, and remaining regions form a set of negative examples. A loss function is computed based on a difference between desired and real output values of the anatomical point detector for detecting anatomical points. The most well-known loss functions are mean-square deviation (MSD) and a negative logarithm of reliability, although it is understood that other loss functions may also be used according to other exemplary embodiments.

The negative logarithm of reliability is defined by Equation (3) below:

$$L(y,q) = -y\log(q) - (1-y)\log(1-q) \quad \text{Equation 3}$$

where y denotes the binary mark value 1 if an input region of an image contains an anatomical point, and 0 if the input region does not contain an anatomical point, and q has a value between 0 and 1 and represents a pseudo-probability, computed by the anatomical point detector, that the region contains an anatomical point.

The drawback of using the loss function during training of the anatomical point detector is that it is impossible to consider a distance from a falsely detected anatomical point to a real anatomical point.

In order to eliminate this drawback, a modified version of a loss function is defined by Equation (4) below:

$$\hat{L}(X, Y, Q, M_x, \Sigma_x) = \sum_{x \in X} L(y_x, q_x) + E(X, M_x, \Sigma_x) \quad \text{Equation (4)}$$

where Y represents a set of marks corresponding to each region of a volume in a 3D medical image, which are defined by x coordinates belonging to a set X, and Q is a set of outputs of the anatomical point detector for each region of the volume.

Figure 3A:
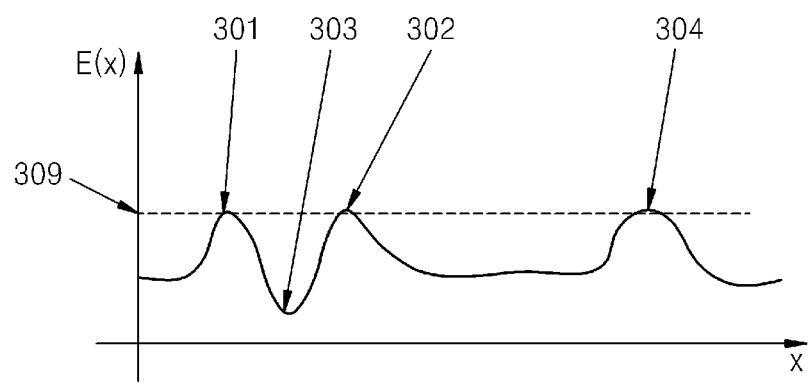
FIGS. 3A and 3B are schematic illustrations of an error surface defined by a standard loss function and a loss function used in an exemplary embodiment.
Figure 3B:
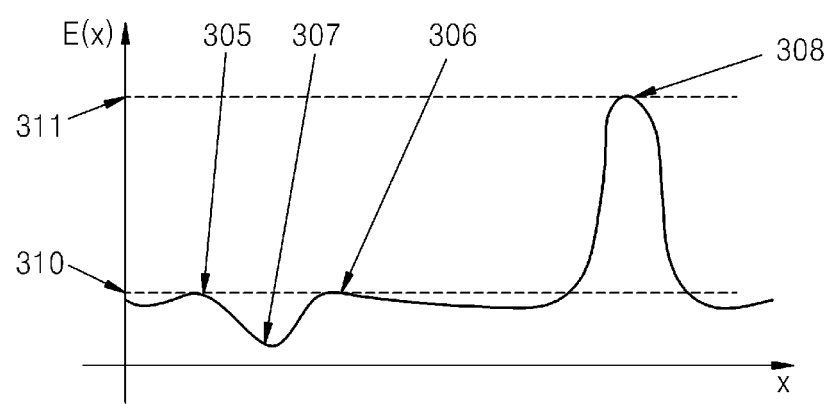

As the matching of a set of the detected anatomical points to a statistical model decreases, a larger loss function value is output. FIGS. 3A and 3B illustrate graphical representations of dependences of functions of losses from coordinates. In FIGS. 3A and 3B, the ordinate (x-axis) and abscissa (y-axis) denote energy of a loss function in the statistical model and a coordinate value, respectively. Minimums 303 and 307 of an error correspond to true detections of anatomical points by the anatomical point detector. In detail, the error may represent a value of a loss function in the statistical model. Peaks 301, 302, 305 and 306 correspond to falsely detected points located close to a true position of an anatomical point. Peaks 304 and 308 correspond to falsely detected points located far from a true position of an anatomical point. It is evident from FIGS. 3A and 3B that when the loss function defined by Equation (3) above is used, an error value 309 for false detection near the true position of the anatomical point is the same as for false detection at points farther away from the true position thereof. Conversely, when the loss function defined by Equation (4) is used, considering the global statistics of mutual positions of anatomical points, a loss function value corresponding to the point 308, located far from the true position of an anatomical point, is more than a loss function value corresponding to a point close to 310.

Search of an Optimum Configuration of Anatomical Points.

The result of detection of anatomical points in a set region of a volume may be represented as an m-vector $Q=(q_1, \ldots, q_m)$ that sets pseudo-probabilities of the presence of each of m key points in the volume. During detection of candidates of anatomical points at operation 104, such a procedure is performed for each point from a set $P=(p_1, \ldots, p_n)$ which can represent a set of all points of the volume or some subset of the points. Thus, m-vector $Q_i$ is input in response to each point $p_i$. In a simple case, the required configuration of anatomical points may be determined as m points $\hat{p}_1, \ldots, \hat{p}_m$ having a maximum value of a corresponding element of vector Q. However, when an initial image is of low quality, there may be an error or anatomical deviations from the norm, the anatomical point detector can be mistaken, and a point with a maximum pseudo-probability for the given type of an anatomical point may be far from a true position of this point.

Figure 4:
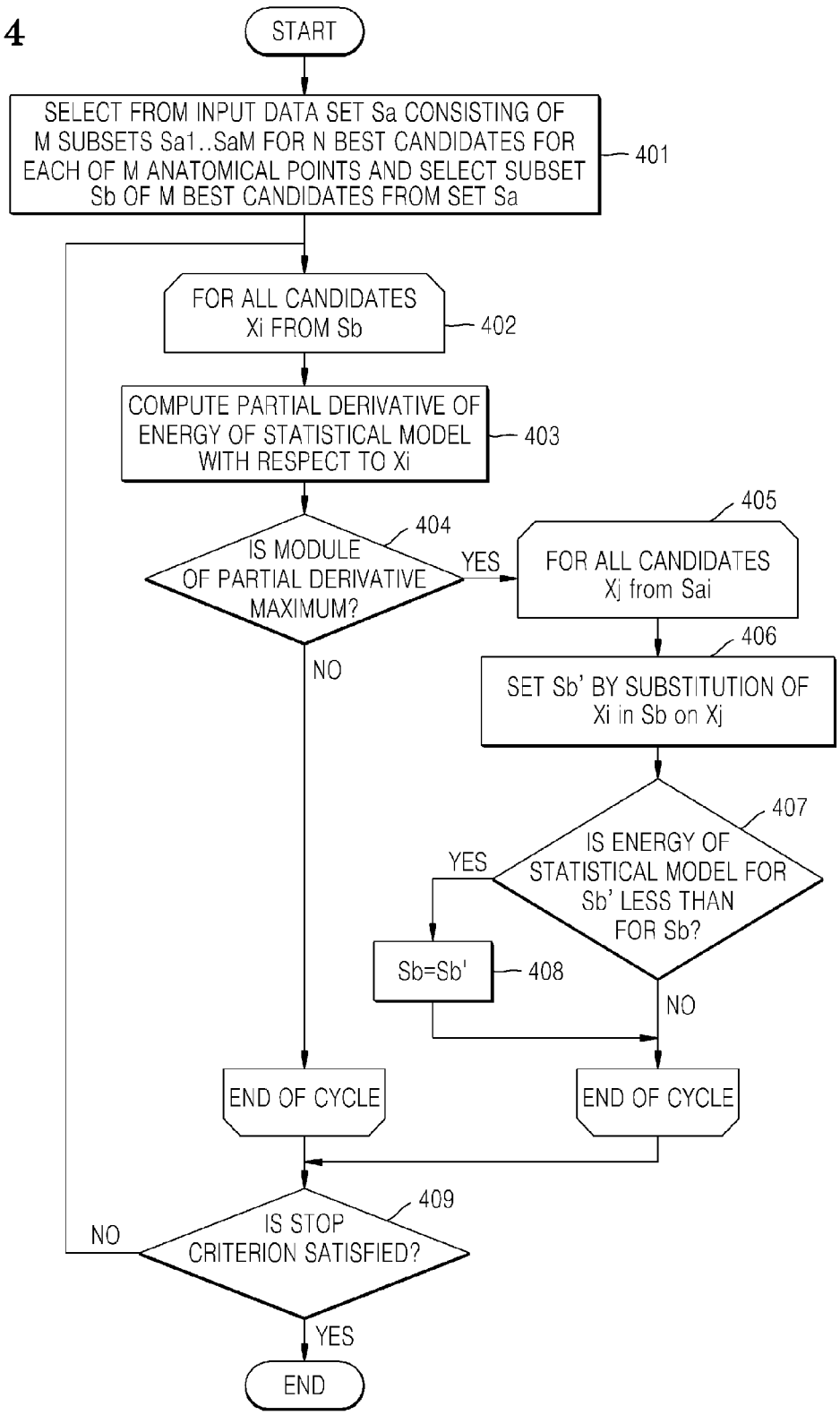
FIG. 4 illustrates a greedy iterative algorithm for finding an optimum configuration of anatomical points according to an exemplary embodiment.

To overcome the above specified problem, according to exemplary embodiments, a greedy iterative search may be performed to find a configuration that minimizes energy of the statistical model. FIG. 4 is a flowchart of a greedy iterative search.

According to an exemplary embodiment, a set $S_a$ consisting of M subsets $S_{a1} \ldots S_{aM}$ of N candidates and having the largest value of a pseudo-probability belonging to each of M anatomical points is selected from a set of candidates of anatomical points at operation 401. A subset $S_b$ of M best candidates is also selected from among the set $S_a$, one candidate for each of anatomical points. Further, a partial derivative $$\frac{\partial E(X, M_x, \Sigma_x)}{\partial x_i}$$

of a statistical model with respect to all candidates $x_i$ is calculated in a cycle by all the candidates $x_i$ from $S_b$ at operations 402 and 403. When a module of a partial derivative for a given element is a maximum among modules of partial derivatives for elements of the subset $S_b$ at operation 404, an internal cycle starts for all candidates $x_j$ from $S_{ai}$ at operation 405. A new configuration $S_b'$ is determined by substitution of $x_i$ in subset $S_b$ instead of $x_j$ at operation 406. The new configuration $S_b'$ is used for computing energy of the statistical model. If the energy is determined to be less than the energy for subset $S_b$ at operation 407, $S_b$ is assigned a value of $S_b'$ at operation 408. The above-described process is iteratively performed until satisfaction of a certain set stop criterion at operation 409, where the set stop criterion may be, for example, a maximum number of iterations or the minimum value of the module of partial derivative.

Coordinates of view planes are computed based on the detected optimum configuration of anatomical points at operation 106.

System for Automatically Planning Views in 3D Medical Images.

Figure 5:
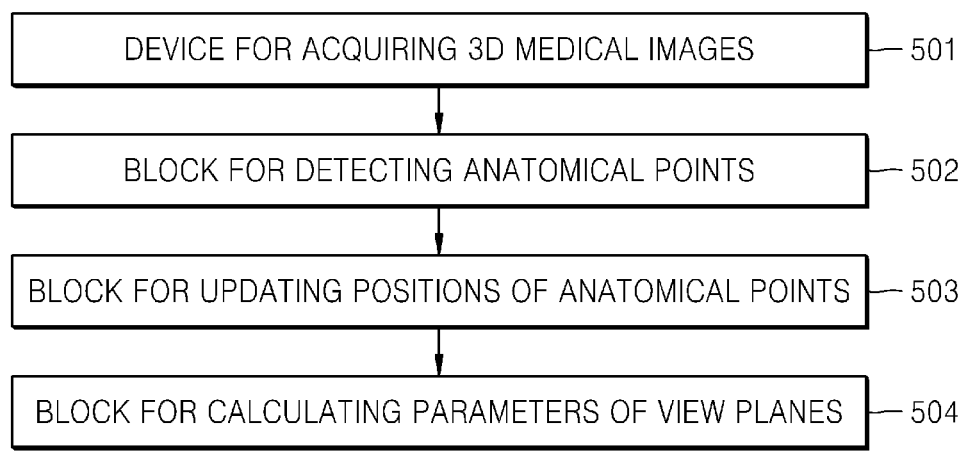
FIG. 5 illustrates a system for automatically planning views in 3D medical images according to an exemplary embodiment.

FIG. 5 illustrates a system for automatically planning views in 3D medical images according to an exemplary embodiment. Referring to FIG. 5, the system includes an image acquisition device 501 for acquiring 3D medical pictures. For example, the image acquisition device 501 may be implemented as an MRT, a CT or any other type of device configured to reconstruct 3D images. An image from the image acquisition device 501 is input to an anatomical point detection block 502 which implements an algorithm for detecting anatomical points as described above. The anatomical point detection block 502 is trained using the approach described above. Outputs of the anatomical point detection block 502 are input to a position updating block 503 for updating positions of anatomical points for which a search algorithm is performed to find the best configuration of the anatomical points. Outputs of the position updating block 503 are input to a parameter calculation block 504 for calculating parameters of view planes which implement an algorithm for transforming coordinates in parameters of target views.

An exemplary embodiment may provide a carrier of information containing instructions, to be executed by a computer, for automatic planning of views in 3D medical images. The information carrier may be a type of media having information recorded thereon. A central processing unit (CPU) of a computer may execute instructions for estimating parameters of a statistical model of relative positions of anatomical points, for training of an anatomical point detector using energy of a statistical model as a part of a loss function, for acquiring a 3D image of a region of interest, for detecting a set of candidates of anatomical points using the anatomical point detector, for detecting the best configuration of anatomical points using a greedy iterative search of a configuration that minimizes the energy of the statistical model, and for computing coordinates of view planes based on the found configuration of anatomical points.

The system and method for automatically planning views in 3D images according to the exemplary embodiments may be applicable to any medical imaging devices capable of acquiring 3D images, such as an MRT, a CT, a single-photon emission computed tomography (SPECT), a device employing photoacoustic tomography (PAT), elastography devices, etc. Furthermore, the system and method may be used for the organization and visualization of medical image databases.

Examples of the above-described systems according to exemplary embodiments include a processor, a memory for storing and executing program data, a permanent storage such as a disc drive, a communications port for handling communications with external devices, and a user interface device such as a touch panel, keys or buttons. When software modules or algorithms are implemented, these software modules or algorithms may be stored as program instructions or computer readable codes executable by the processor on a non-transitory computer-readable media. Examples of the computer-readable media may include magnetic storage media (e.g., read-only memory (ROM), random-access memory (RAM), floppy disks, hard disks, etc.) and optical recording media (e.g., CD-ROM, Digital Versatile Disc (DVD), etc.). The computer readable recording media may also be distributed over network coupled computer systems so that the computer readable codes are stored and executed in a distributed fashion. These media can be read by the computer, stored in the memory, and executed by the processor.

The present exemplary embodiments may be described in terms of functional block components and various processing steps. Such functional blocks may be realized by any number of hardware and/or software components configured to perform the specified functions. For example, the exemplary embodiments may employ various integrated circuit components, e.g., memory elements, processing elements, logic elements, look-up tables, and the like, which may carry out a variety of functions under the control of one or more microprocessors or other control devices. Similarly, where the elements of the exemplary embodiments are implemented using software programming or software elements, the exemplary embodiments may be implemented with any programming or scripting language such as C, C++, Java, assembler, or the like, with the various algorithms being implemented with any combination of data structures, processes, routines or other programming elements. Functional aspects may be implemented in algorithms that execute on one or more processors. Furthermore, the exemplary embodiments may employ any number of conventional techniques for electronics configuration, signal processing and/or data processing and the like. The words "mechanism," "element," "means," and "construction" are used broadly and are not limited to mechanical or physical exemplary embodiments, but may include software routines in conjunction with processors, etc.

The particular implementations shown and described herein are illustrative examples of the exemplary embodiments and are not intended to otherwise limit the scope of the disclosure in any way. For the sake of brevity, conventional electronics, control systems, software development, and other functional aspects of the systems may not be described in detail. Furthermore, the connecting lines, or connectors shown in the various figures, are intended to represent exemplary functional relationships and/or physical or logical couplings between the various elements. It should be noted that many alternative or additional functional relationships, physical connections or logical connections may be present in a practical device.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the e present invention as defined by the following claims.

What is claimed is:

1. A method for automatically planning views in three-dimensional (3D) medical images, the method comprising:
   estimating a statistical model indicating positions of a plurality of anatomical points, the statistical model having parameters calculated by minimizing energy of a loss function, wherein the loss function outputs error values for the plurality of anatomical points, the error values indicating whether the plurality of anatomical points are falsely detected anatomical points or real anatomical points;
   training an anatomical point detector to detect the plurality of anatomical points by using the estimated statistical model;
   acquiring a 3D image having a region of interest;
   detecting a set of candidates of the plurality of anatomical points in the 3D image;
   searching the set of candidates for an optimal configuration corresponding to the plurality of anatomical points; and
   forming a view plane based on the optimal configuration found by the searching.

2. The method of claim 1, wherein the estimating of the statistical model is performed using an annotated set of the 3D medical images.

3. The method of claim 1, wherein the training of the anatomical point detector is performed using energy of the estimated statistical model and is performed only a single time before performing the acquiring.

4. The method of claim 1, wherein the detecting of the set of candidates of the plurality of anatomical points is performed by the anatomical point detector trained using an algorithm based on the plurality of anatomical points.

5. The method of claim 1, wherein the searching the set of candidates for the optimal configuration corresponding to the plurality of anatomical points comprises performing a greedy iterative search to search for a configuration that minimizes energy of the estimated statistical model.

6. The method of claim 3, wherein the energy of the loss function in the statistical model is determined by using the equation:

$$E(X, M_x, \Sigma_x) = \sum_{x_s \in X, x_t \in X} \psi_{st}(x_s, x_t, M_x, \Sigma_x)$$

in which $X \in R^{a \times m}$ is a set of M vectors of coordinates of the plurality of anatomical points, which are a configuration of anatomical points, $M_X$ is a mathematical expectation of distances of the plurality of anatomical points from each other, $\Sigma_X$ is a tensor of covariance of distances between the plurality of anatomical points, E is the energy of the estimated statistical model, wherein as values of the energy E become smaller, the values match more closely with the configuration of the anatomical points, and $\psi_{st}$ is a function of spatial energy that measures a statistical coordination of coordinates of two anatomical points.

7. The method of claim 6, wherein the spatial energy is determined by using the equation:

$$\psi_{st}(x_s, x_t, M_X, \Sigma_X) = 0.5(x_s - x_t - \mu_{st})^T \Sigma_{st}^{-1}(x_s - x_t - \mu_{st})$$

in which $x_s$ and $x_t$ are vectors of coordinates in a 3D space acquired from the configuration of anatomical points x, and $\mu_{st}$ is a three-element vector from the point s to the point t, which is a return matrix of a covariance of 3D vectors between the points s and t.

8. The method of claim 1, wherein parameters of the anatomical point detector are computed by minimizing the loss function determined by using the equation:

$$\hat{L}(X, Y, Q, M_x, \Sigma_x) = \sum_{x \in X} L(y_x, q_x) + E(X, M_x, \Sigma_x)$$

in which Y denotes a binary mark taking a value of 1 if an input region of an image contains an anatomical point, and 0 if the input region does not contain an anatomical point, q has a value between 0 and 1 and represents a pseudo-probability, computed by the anatomical point detector, that the region contains an anatomical point, Yx and Qx are values of Y or Q at a coordinate point x, and 'x' is a space position or coordinates of all voxels in a volume.

9. The method of claim 5, wherein the performing of the greedy iterative search to search for the configuration that minimizes the energy of the statistical model comprises:
selecting a set $S_a$ consisting of M subsets $S_{a1} \ldots S_{aM}$ of N best candidates for each of M anatomical points;
selecting a subset $S_b$ of M best candidates from the set $S_a$;
calculating a partial derivative of the energy of the statistical model with respect to coordinates of each element from the subset $S_b$; and
searching a subset $S_{ai}$ for an element $x_j$ that minimizes the energy of the statistical model.

10. A medical system configured to automatically plan views in three-dimensional (3D) medical images, the medical system comprising:
an image acquiring device configured to acquire the 3D medical images;
a detecting device configured to detect anatomical points by using a statistical model having parameters calculated by minimizing energy of a loss function that is determined by using the equation:

$$\hat{L}(X, Y, Q, M_x, \Sigma_x) = \sum_{x \in X} L(y_x, q_x) + E(X, M_x, \Sigma_x)$$

in which Y denotes a binary mark taking a value of 1 if an input region of an image contains an anatomical point, and 0 if the input region does not contain an anatomical point, q has a value between 0 and 1 and represents a pseudo-probability, computed by an anatomical point detector, that the region contains an anatomical point, Yx and Qx are values of Y or Q at a coordinate point x, and 'x' is a space position or coordinates of all voxels in a volume;
an updating device configured to update the anatomical points by performing a search algorithm for finding an optimal configuration of the anatomical points; and
a calculation device configured to acquire parameters of a view plane by applying parameters of a target view to an algorithm for transforming coordinates,
wherein outputs of the detecting device that are positions of the anatomical points are input to the updating device, and
wherein outputs of the updating device are input to the calculation device.

11. A non-transitory computer readable recording medium storing a program which, when executed, causes a computer to perform a method for automatic planning of a view in a three-dimensional (3D) medical image, the method comprising:
estimating parameters of a statistical model of relative positions of anatomical points;
training an anatomical point detector using energy of the statistical model as a part of a loss function, wherein the loss function outputs error values for the anatomical points, the error values indicating whether the anatomical points are falsely detected anatomical points or real anatomical points;
acquiring a 3D image having a region of interest;
detecting a set of candidates of the anatomical points in the 3D image using the anatomical point detector;
detecting an optimal configuration of the anatomical points using a greedy iterative search to search for a configuration that minimizes the energy of the statistical model, and
computing coordinates of view planes based on the detected optimal configuration.

12. The non-transitory computer readable recording medium of claim 11, wherein the energy of the statistical model is determined by using the equation:

$$E(X, M_x, \Sigma_x) = \sum_{x_s \in X, x_t \in X} \psi_{st}(x_s, x_t, M_x, \Sigma_x)$$

in which $X \in R^{a \times M}$ is a set of M vectors of coordinates of the anatomical points, which are a configuration of anatomical points, $M_X$ is a mathematical expectation of distances of the anatomical points from each other, $\Sigma_X$ is a tensor of covariance of distances between the anatomical points, E is the energy of the statistical model, wherein as values of the energy E become smaller, the values match more closely with the configuration of the anatomical points, and $\psi_{st}$ is a function of spatial energy that measures a statistical coordination of coordinates of two anatomical points.

13. The non-transitory computer readable recording medium of claim 12, wherein the spatial energy is determined by using the equation:

$$\psi_{st}(x_s, x_t, M_X, \Sigma_X) = 0.5(x_s - x_t - \mu_{st})^T \Sigma_{st}^{-1}(x_s - x_t - \mu_{st})$$

In which $x_s$ and $x_t$ are vectors of coordinates in a 3D space acquired from the configuration of anatomical points x, and $\mu_{st}$ is a three-element vector from the point s to the point t, which is a return matrix of a covariance of 3D vectors between the points s and t.

14. The non-transitory computer readable recording medium of claim 11, wherein parameters of the anatomical point detector are computed by minimizing the loss function determined by using the equation:

$$\hat{L}(X, Y, Q, M_x, \Sigma_x) = \sum_{x \in X} L(y_x, q_x) + E(X, M_x, \Sigma_x)$$

in which Y denotes a binary mark taking a value of 1 if an input region of an image contains an anatomical point, and 0 if the input region does not contain an anatomical point, q has a value between 0 and 1 and represents a pseudo-probability, computed by the anatomical point detector, that the region contains an anatomical point, Yx and Qx are values of Y or Q at a coordinate point x, and 'x' is a space position or coordinates of all voxels in a volume.

15. The non-transitory computer readable recording medium of claim 12, wherein the detecting the optimal configuration of the anatomical points using the greedy iterative search comprises:
    selecting a set $S_a$ consisting of M subsets $S_{a1} \ldots S_{aM}$ of N best candidates for each of M anatomical points;
    selecting a subset $S_b$ of M best candidates from the set $S_a$;
    calculating a partial derivative of the energy of the statistical model with respect to coordinates of each element from the subset $S_b$; and
    searching a subset $S_{ai}$ for an element $x_j$ that minimizes the energy of the statistical model.

16. A medical system configured to process medical images, the medical system comprising:
    an image acquiring device configured to transmit a signal to an object and acquire 3D medical images based on the transmitted signal;
    a detecting device configured to detect anatomical points within the 3D medical images by using a statistical model as a part of a loss function, wherein the loss function outputs error values for the anatomical points, the error values indicating whether the anatomical points are falsely detected anatomical points or real anatomical points, and to detect an optimum configuration of the detected anatomical points using a greedy iterative search; and
    a display configured to display an image according to the detected optimum configuration.

17. The medical system of claim 16, wherein the display is further configured to transmit the image to an external device.

18. The medical system of claim 16, wherein the greedy iterative search performs a search based on minimizing energy of the statistical model.

19. The medical system of claim 16, wherein the statistical model is determined by analyzing a training sample including a set of the 3D medical images and annotations of anatomical points corresponding to the set of the 3D medical images.

20. The medical system of claim 16, wherein the statistical model is determined by considering spatial relations between the anatomical points.

* * * * *